United States Patent
Harada et al.

(10) Patent No.: US 6,541,636 B2
(45) Date of Patent: Apr. 1, 2003

(54) PROCESS FOR PREPARING QUINOLYLACRYLONITRILE AND INTERMEDIATES THEREFOR

(75) Inventors: Katsumasa Harada, Yamaguchi (JP); Shigeyoshi Nishino, Yamaguchi (JP); Naoko Okada, Yamaguchi (JP); Hidetaka Shima, Yamaguchi (JP); Takashi Harada, Yamaguchi (JP)

(73) Assignees: Ube Industries, Ltd. (JP); Nissan Chemical Industries, Ltd. (JP)

( * ) Notice: Subject to any disclaimer, the term of this patent is extended or adjusted under 35 U.S.C. 154(b) by 0 days.

(21) Appl. No.: 10/181,973

(22) PCT Filed: Jan. 24, 2001

(86) PCT No.: PCT/JP01/00451
§ 371 (c)(1),
(2), (4) Date: Jul. 24, 2002

(87) PCT Pub. No.: WO01/53264
PCT Pub. Date: Jul. 26, 2001

(65) Prior Publication Data
US 2003/0013885 A1 Jan. 16, 2003

(30) Foreign Application Priority Data
Jan. 24, 2000 (JP) ........................................ 2000-014864

(51) Int. Cl.⁷ .............................................. C07D 215/04
(52) U.S. Cl. ...................................... 546/173; 546/176
(58) Field of Search ................................ 546/173, 176

(56) References Cited

U.S. PATENT DOCUMENTS

| 5,008,270 A | * | 4/1991 | Secrist, III et al. | ......... 514/258 |
| 5,286,721 A | * | 2/1994 | Murata et al. | ............... 514/210 |
| 6,335,449 B1 | * | 1/2002 | Ohara et al. | ................. 546/173 |

* cited by examiner

Primary Examiner—Patricia L. Morris
(74) Attorney, Agent, or Firm—Nixon Peabody LLP; Jeffrey L. Costellia

(57) ABSTRACT

3-[2-Cyclopropyl-4-(4-fluorophenyl)-3-quinolyl]prop-2-enenitrile is prepared by reacting 2-cyclopropyl-4-(4-fluorophenyl)quinoline-3-carbaldehyde with acetonitrile in the presence of a base and then adding a dehydrating to the reaction mixture to conduct dehydration. Under ordinary conditions, novel 3-[2-cyclopropyl-4-(4-fluoro-phenyl)-quinolin-3-yl]-3-hydroxypropionitrile is formed as an intermediate in the above reaction. Incidentally, when the above reaction is conducted in an organic solvent, 3-[2-cyclopropyl-4-(4-fluorophenyl)-3-quinolyl]-prop-2-enenitrile is directly formed.

20 Claims, No Drawings

PROCESS FOR PREPARING QUINOLYLACRYLONITRILE AND INTERMEDIATES THEREFOR

TECHNICAL FIELD

The present invention relates to a process for preparing a quinolylacrylonitrile derivative from a quinolinecarbaldehyde derivative. The quinolylacrylonitrile derivative produced by the method of the invention is employable as a starting compound for the preparation of a quinolylpropenal derivative which is utilizable for the synthesis of a cholesterol reducing agent (HMG-CoA reductase inhibitor).

BACKGROUND ART

Until now, it has been known that the quinolylpropenal derivative is prepared by the two step process comprising a step of reducing a quinoline acrylate by diisobutylaluminum hydride to give quinolylpropenol and a subsequent step of oxidizing the quinolylpropenol by the use of a combination of oxalyl chloride and dimethylsulfoxide, or manganese dioxide (J. Med. Chem., 34, 367 (1991)).

Further known is a method of selectively reducing the cyano group to a formyl group by the use of a diisobutylaluminum hydride reducing agent, keeping the double bond of an acrylonitrile compound to produce a propenal compound (Heterocycles, 29, 691(1989)).

Both of the above-mentioned process and method are disadvantageous from the viewpoint of industrial preparation because these process and method utilize iisobutylaluminum hydride or manganese dioxide which requires careful handling procedures and complicated post-treatment.

DISCLOSURE OF THE INVENTION

The present invention resides in a process for preparing 3-[2-cyclopropyl-4-(4-fluorophenyl)-3-quinolyl]-prop-2-enenitrile which comprises the steps of reacting 2-cyclopropyl-4-(4-fluorophenyl)quinoline-3-carbaldehyde with acetonitrile in the presence of a base to produce a mixture of 3-[2-cyclopropyl-4-(4-fluorophenyl)-3-quinolyl] prop-2-enenitrile and 3-[2-cyclopropyl-4-(4-fluoro-phenyl) quinolin-3-yl]-3-hydroxypropionitrile; and dehydrating the mixture in the presence of a dehydrating agent.

The starting compound of the reaction of the invention, that is, 2-cyclopropyl-4-(4-fluorophenyl)quinoline-3-carbaldehyde [hereinafter referred to as quinolinecarbaldehyde derivative], the intermediate product, that is, 3-[2-cyclopropyl-4-(4-fluorophenyl)quinolin-3-yl]-3-hydroxypropionitrile [hereinafter referred to as quinolylhydroxypropionitrile derivative], and the desired compound, that is, 3-[2-cyclopropyl-4-(4-fluorophenyl)-3-quinolyl]prop-2-enenitrile [hereinafter referred to as quinolylacrylonitrile derivative] are the compounds represented, respectively, by the following formulas (1), (2), and (3):

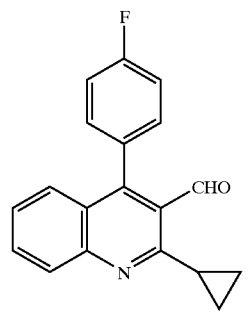

(1)

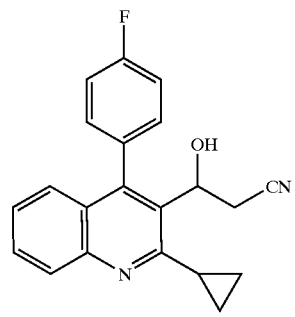

(2)

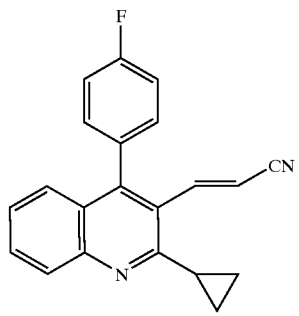

(3)

The invention further resides in the above-mentioned 3-[2-cyclopropyl-4-(4-fluorophenyl)-3-quinolin-3-yl]-3-hydroxypropionitrile.

The invention furthermore resides in a process for preparing 3-[2-cyclopropyl-4-(4-fluorophenyl)-3-quinol-yl] prop-2-enenitrile which comprises the steps of reacting 2-cyclopropyl-4-(4-fluorophenyl)quinoline-3-carbaldehyde with acetonitrile in the presence of a base; and dehydrating the resulting product in the presence of a dehydrating agent.

The invention furthermore resides in a method for preparing 3-[2-cyclopropyl-4-(4-fluorophenyl)-3-quinolyl] prop-2-enenitrile which comprises reacting 2-cyclopropyl-4-(4-fluorophenyl)quinoline-3-carbaldehyde with acetonitrile in an organic solvent in the presence of a base.

The quinolylacrylonitrile derivative of the formula (3) {i.e., 3-[2-cyclopropyl-4-(4-fluorophenyl)-3-quinolyl]prop-2-enenitrile} obtained by the invention can be converted into 3-[2-cyclopropyl-4-(4-fluorophenyl)-3-quinolyl]prop-2-enal by reducing the derivative using a Raney-nickel in the presence of a combination of formic acid and water [in an amount of 0.25 to 1 volume part per one volume part of the formic acid].

DETAILED DESCRIPTION OF THE INVENTION

The 2-cyclopropyl-4-(4-fluorophenyl)quinoline-3-carbaldehyde of the formula (1) which is the starting material of the reaction of the invention is described in JP-A-1-279866, EP-A-304063, and U.S. Pat. No. 5,011,930, and is already known.

Examples of the bases employed in the reaction of the invention include a metal hydride such as lithium hydride, sodium hydride, potassium hydride, or calcium hydride; a metal amide such as lithium amide, sodium amide, lithium diisopropylamide, lithium bis(trimethylsilyl)amide, or potassium bis(trimethylsilyl)amide; a metal alkoxide such as sodium methoxide, sodium ethoxide, sodium t-butoxide, potassium t-butoxide, magnesium methoxide, or magnesium ethoxide; an alkyl lithium such as methyllithium, butyllithium, or t-butyllithium; or a metal hydroxide such as lithium hydroxide, sodium hydroxide, potassium hydroxide, or calcium hydroxide. Preferred are a metal hydride, a metal alkoxide, and a metal hydroxide. More preferred are a metal hydride and a metal alkoxide.

The base is employed in an amount of preferably 0.9 to 3.0 moles, more preferably 1.0 to 2.0 moles, per one mole of the starting compound, i.e., the quinolinecarbaldehyde derivative.

In the reaction, the acetonitrile is employed in an amount of preferably 0.9 to 100 moles, more preferably 1.0 to 60 moles, per one mole of the starting compound, i.e., the quinolinecarbaldehyde derivative.

In the reaction, the dehydrating agent functions to dehydrate the below-mentioned quinolylhydroxypropionitrile derivative having a hydroxyl group which is probably produced in the reaction as an intermediate product to give the desired product [quinolylacrylonitrile derivative having a double bond] according to the below-illustrated reaction (4):

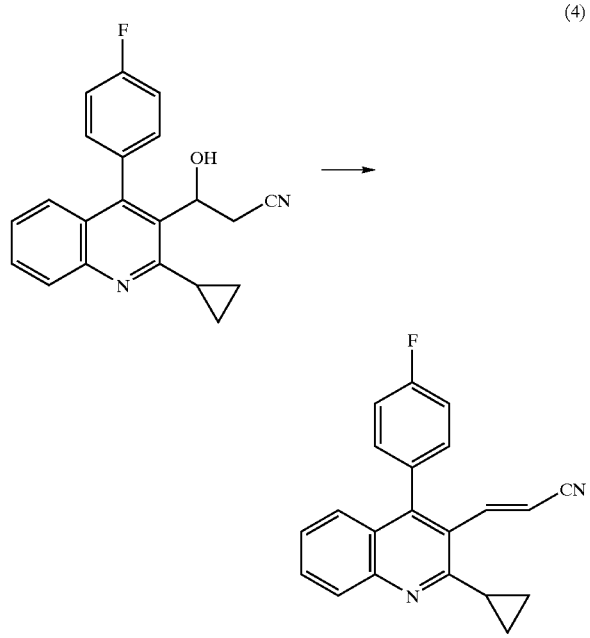

(4)

Examples of the dehydrating agents include inorganic acids such as hydrochloric acid and sulfuric acid; organic acids such as formic acid, acetic acid, and trifluoroacetic acid; organic acid esters such as methyl formate, ethyl formate, propyl formate, butyl formate, and ethyl acetate; amides such as N,N-dimethylformamide; organic acid anhydrides such as acetic anhydride and trifluoroacetic anhydride; acid chlorides such as mesyl chloride, thionyl chloride, and acetyl chloride; tertiary amines such as trimethylamine, triethylamine, ethyldiisopropylamine, diethylisopropylamine, and benzyldimethylamine; and silane compounds such as 1,1,1,3,3,3-hexamethyldisilazane. Preferred are organic acid esters and a combination of an acid chloride and a tertiary amine. More preferred are organic acid esters. Most preferred are formic acid esters. The dehydrating agent is employed in an amount of preferably 0.1 to 100 moles, more preferably 0.2 to 50 moles per one mole of the starting compound, i.e., the quinolinecarbaldehyde derivative.

The reaction of the invention can be carried out by reacting the quinolinecarbaldehyde derivative and acetonitrile in the presence of a base to produce a mixture of the quinolylhydroxypropionitrile derivative (intermediate product) and the quinolylacrylonitrile derivative (desired product), and completing the reaction upon addition of a dehydrating agent at an atmospheric pressure or an increased pressure. The reaction temperature is in the range of, preferably, $-78°$ C. to $80°$ C., more preferably $-30°$ C. to $50°$ C.

The reaction of the starting compounds (guinolinecarbaldehyde derivative and acetonitrile) in the presence of a base can be carried out in an organic solvent to produce directly (this means "without utilizing a dehydrating agent") the desired product. The organic solvent is one other than the acetonitrile.

The organic solvent preferably has a dielectric constant of 10 or less in the temperature range of 20 to $25°$ C. (at an optionally selected temperature in this range). The details of "dielectric constant" are described in "Chemistry Handbook, Basic Issue, 4th edition (II)" (Maruzen Publishing), and "Solvent Handbook, 1st edition" (Kodansha Scientific). Examples of the organic solvents include aliphatic solvents such as hexane, heptane, cyclohexane, methylene chloride, chloroform, and carbon tetrachloride; aromatic solvents such as benzene, toluene, xylene, chlorobenzene and dichlorobenzene; and ether solvents such as methylal, tetrahydrofuran, and dioxane. Preferred are aromatic solvents and ether solvents. More preferred are aromatic solvents. Most preferred is toluene. The organic solvents can be employed singly or in combination.

The organic solvent can be employed in an amount of preferably 0.5 to 50 weight parts, more preferably 1 to 20 weight parts, per one weight part of the quinolinecarbaldehyde derivative (starting compound).

The reaction can be carried out by reacting the quinolinecarbaldehyde derivative and acetonitrile at an atmospheric pressure or an increased pressure in an organic solvent in the presence of a base. The reaction temperature is in the range of preferably 30 to $140°$ C., more preferably 40 to $120°$ C.

In the reaction utilizing an organic solvent, the base is employed in an amount of preferably 0.5 to 3.0 moles, more preferably 0.8 to 2.0 moles, per one mole of the quinolinecarbaldehyde derivative. (starting compound).

In the reaction utilizing an organic solvent, acetonitrile is employed in an amount of preferably 0.9 to 50 moles, more preferably 1.0 to 30 moles, per one mole of the quinolinecarbaldehyde derivative (starting compound). The reaction product (desired product) of the reactions of the invention, that is, quinolylacrylonitrile derivative can be isolated and purified after the reaction is complete, by a conventional procedure such as recrystallization or column chromatography.

EXAMPLE 1

Preparation of 3-[2-Cyclopropyl-4-(4-fluorophenyl)-3-quinolyl]prop-2-enenitrile

In a 100 mL-volume glass flask equipped with a stirrer, a thermometer and a dropping funnel were placed under argon atmosphere 1.94 g (6.66 mmol) of 2-cyclo-propyl-4-(4-fluorophenyl)quinoline-3-carbaldehyde, 10 mL of acetonitrile and 0.422 g (10.6 mmol). of sodium hydride (purity: 60%). The content was stirred at room temperature for 2 hours. The resulting mixture was chilled to −10° C. To the chilled mixture was added 20 mL (248 mmol) of ethyl formate, and the mixture was stirred for 4 hours at the same temperature. Subsequently, to the mixture was slowly added 11 mL of hydrochloric acid (1 mol/L) which was previously chilled in an ice bath. In the mixture, an organic portion separated from an aqueous portion. The organic portion was taken out, washed with two 10 mL portions of saturated aqueous sodium chloride solution, and dried over anhydrous magnesium sulfate. The organic portion was filtered and analyzed by high performance liquid chromatography (absolute quantitative analysis). It was confirmed that 1.71 g (yield: 85%) of 3-[2-cyclopropyl-4-(4-fluorophenyl)-3-quinolyl]prop-2-enenitrile was produced. The organic portion was concentrated under reduced pressure to leave a yellow solid residue. The solid residue was recrystallized from toluene/hexane (1/8, vol. ratio) to obtain 1.79 g of 3-[2-cyclopropyl-4-(4-fluorophenyl)-3-quinolyl]prop-2-enenitrile as a yellow crystalline product (purity: 97%). The obtained 3-[2-cyclopropyl-4-(4-fluorophenyl)-3-quinolyl]prop-2-enenitrile had the following characteristics:

m.p.: 174.5–175.0° C.; EI-MS(m/e): 314(M), CI-MS(m/e): 315(M+1); IR (KBr, cm$^{-1}$): 2223, 1513, 1490, 1224, 1161, 846, 768. Elementary analysis: C 80.31%, H 4.74%, N 8.89%. (theoretical value for $C_{21}H_{15}N_2F$: C, 80.24%, H, 4.81%, N, 8.91%) $^1$H-NMR (CDCl$_3$, δ(ppm)): 1.06–1.15 (2H, m), 1.36–1.46 (2H, m), 2.23–2.33 (1H, m), 5.29 (1H, d, J=17.0 Hz), 7.18–7.32 (4H, m), 7.34–7.39 (1H, m), 7.52 (1H, d, J=17.0 Hz), 7.60–7.73 (1H, m), 7.97 (1H, d, J=8.3 Hz).

EXAMPLE 2

Preparation of 3-[2-Cyclopropyl-4-(4-fluoro-phenyl)-3-quinolyl]prop-2-enenitrile In a flask similar to that employed in Example 1 were placed under argon atmosphere 1.96 g (6.73 mmol) of 2-cyclopropyl-4-(4-fluorophenyl)quinoline-3-carbaldehyde, 10 mL of acetonitrile and 0.434 g (10.9 mmol) of sodium hydride (purity: 60%). The content was stirred at room temperature for 2 hours. The resulting mixture was chilled to 0° C. To the chilled mixture was added 0.85 mL (10.5 mmol) of ethyl formate, and the mixture was stirred for 4 hours at the same temperature. Subsequently, to the mixture was slowly added 10 mL of chilled water. The mixture was then extracted with 30 mL of ethyl acetate which was previously chilled in an ice bath. The organic portion was dried over anhydrous magnesium sulfate, and filtered. The filtrate was analyzed by high performance liquid chromatography (absolute quantitative analysis). It was confirmed that 1.74 g (yield: 82%) of 3-[2-cyclo-propyl-4-(4-fluorophenyl)-3-quinolyl]prop-2-enenitrile was produced.

EXAMPLE 3

Preparation of 3-[2-Cyclopropyl-4-(4-fluoro-phenyl)-3-quinolyl]prop-2-enenitrile In a 50 ml-volume glass flask equipped with a stirrer and a thermometer were placed under argon atmosphere 200 mg (0.69 mmol) of 2-cyclopropyl-4-(4-fluorophenyl)-quinoline-3-carbaldehyde, 2 mL of acetonitrile and 41.5 mg (1.04 mmol) of sodium hydride (purity: 60%). The content was stirred at room temperature for 2 hours. The resulting mixture was chilled to 0° C. To the chilled mixture were added 0.08 mL (1.03 mmol) of methanesulfonyl chloride and 0.15 mL (1.08 mmol) of triethylamine, and the mixture was stirred for 3 hours at the same temperature. Subsequently, to the mixture was added 5 mL of chilled water, and the mixture was extracted with three portions of ethyl acetate (15 mL) which were previously chilled in an ice bath. The mixture was dried over anhydrous magnesium sulfate. The organic portion was then filtered, and the filtrate was analyzed by high performance liquid chromatography (absolute quantitative analysis). It was confirmed that 180 mg (yield: 83%) of 3-[2-cyclopropyl-4-(4-fluorophenyl)-3-quinolyl]prop-2-enenitrile was produced.

EXAMPLE 4

Preparation of 3-[2-Cyclopropyl-4-(4-fluoro-phenyl) quinolin-3-yl]-3-hydroxypropionitrile In a 50 mL-volume glass flask equipped with a stirrer and a thermometer were placed under argon atmosphere 0.20 g (0.68 mmol) of 2-cyclopropyl-4-(4-fluorophenyl)-quinoline-3-carbaldehyde, 2 mL of acetonitrile and 0.042 g (1.06 mmol) of sodium hydride (purity: 60w). The content was stirred at room temperature for 2 hours. The resulting mixture was chilled to 0° C. To the chilled mixture was added 0.08 mL (1.40 mmol) of acetic acid, and the mixture was stirred for 5 minutes at the same temperature. Subsequently, to the mixture was added 10 mL of chilled water, and the mixture was extracted with 20 mL of ethyl acetate which were previously chilled in an ice bath. The organic portion was washed successively with 5 mL of saturated aqueous sodium hydrogen carbonate solution and 5 mL of saturated aqueous sodium chloride solution, and dried over anhydrous magnesium sulfate. The organic portion was then filtered and concentrated under reduced pressure. The concentrate was purified by silica gel column chromatography [column Wakogel C-200, available from Wako Junyaku Co., Ltd., eluent: ethyl acetate/hexane (7/93→15/85, vol. ratio)] to give 0.17 g (yield 75%) of 3-[2-cyclopropyl-4-(4-fluoro-phenyl)quinolin-3-yl]-3-hydroxypropionitrile as white solid.

The obtained 3-[2-cyclopropyl-4-(4-fluorophenyl)-quinolin-3-yl]-3-hydroxypropionitrile had the following characteristics:

m.p.: 200° C.; EI-MS(m/e): 332(M), CI-MS(m/e): 333 (M+1); IR (KBr, cm$^{-1}$): 3496, 2253, 1512, 1491, 1226, 1078, 778. Elementary analysis: C, 75.90%, H, 5.17%, N, 8.39% (theoretical value for $C_{21}H_{17}N_2OF$: C, 75.89%, H, 5.16%, N, 8.43%), $^1$H-NMR (CDCl$_3$, δ(ppm)): 1.07–1.17 (3H, m), 1.79–1.84 (1H, m), 2.48 (1H, d, J=4.2 Hz), 2.87–2.96 (1H, m), 3.01 (1H, dd, J=6.6, 16.9 Hz), 3.26 (1H, dd, J=8.6, 16.9 Hz), 5.25–5.35 (1H, m), 7.12–7.36 (6H, m), 7.63 (1H, m), 7.94 (1H, d, J=8.6 Hz). $^1$H-NMR (CDCl$_3$, δ(ppm)): 1.07–1.20 (3H, m), 1.76–1.84 (1H, m), 2.87–2.96 (1H, m), 3.00 (1H, dd, J=6.6, 16.9 Hz), 3.26 (1H, dd, J=8.6, 16.9 Hz), 5.27 (1H, dd, J=6.6, 8.6 Hz), 7.11–7.36 (6H, m), 7.64 (1H, m), 7.94 (1H, d, J=9.0Hz).

Reference Example 1

Preparation of 3-[2-Cyclopropyl-4-(4-fluorophenyl)-3-quinolyl]prop-2-enal

In a 5 mL-volume glass flask equipped with a stirrer, a thermometer and a dropping funnel were placed under nitrogen atmosphere 314 mg (1.0 mmol) of 3-[2- cyclopropyl-4-(4-fluorophenyl)-3-quinolyl]prop-2-enenitrile (prepared in Example 1), 2.25 mL of formic acid (60 mmol, mol calculated as 100% formic acid), 0.75 mL of water, and 620 mg (5.3 mmol as nickel atom) of water-containing developed Raney-nickel (NDHT-90, nickel content 50 wt. %, available from Kawaken Fine Chemical Co., Ltd.). The content was reacted at 80° C. for 1.5 hours. After the reaction was complete, the content was cooled to room temperature. After addition of 9 mL of water and 9 mL of hydrochloric acid (1 mol/L), the catalyst was removed by filtration using a celite. The celite was washed with two portions of 2-butanol (1 mL) and two portions of toluene (9 mL). The organic portion was dried over anhydrous magnesium sulfate. The dried organic portion was filtered and the filtrate was concentrated under reduced pressure to give 307 mg (yield 91%) of 3-[2-cyclopropyl-4-(4-fluorophenyl)-3-quinolyl]prop-2-enal as yellow solid (purity 97%, in terms of an area percent according to high performance liquid chromatography).

The obtained 3-[2-cyclopropyl-4-(4-fluorophenyl)-3-quinolyl]prop-2-enal had the following characteristics:

CI-MS(m/e): 318(M+1); $^1$H-NMR (CDCl$_3$, δ(ppm)): 1.07–1.13 (2H, m), 1.40–1.45 (2H, m), 2.32–2.37 (1H, m), 6.43 (1H, dd, J=7.8, 16.2 Hz), 7.22–7.26 (4H, m), 7.35–7.38 (2H, m), 7.55 (1H, d, J=16.2 Hz), 7.644–7.69 (1H, m), 7.97 (1H, d, J=8.4 Hz), 9.51 (1H, d, J=7.5 Hz).

EXAMPLE 5

Preparation of 3-[2-cyclopropyl-4-(4-fluorophenyl)-3-quinolyl]prop-2-enenitrile

In a 200 mL-volume glass flask equipped with a stirrer and a thermometer were placed under argon atmosphere 9.2 g (31.6 mmol) of 2-cyclopropyl-4-(4-fluorophenyl)-quinoline-3-carbaldehyde, 7.5 mL (143 mmol) of acetonitrile, 45 mL of toluene (dielectric constant at 25° C.: 2.38), and 1.99 g (36.8 mmol) of sodium methoxide. The content was reacted at 50° C. for 8 hours. The resulting mixture was chilled in an ice bath. To the chilled mixture were slowly added under stirring 40 mL of toluene and 34.0 mL (34.0 mmol) of hydrochloric acid (1 mol/L), successively. The separated organic portion was taken out. After washing with 30 mL of saturated aqueous sodium chloride solution, the organic portion was dried over anhydrous magnesium sulfate. The organic portion was then filtered and analyzed by high performance liquid chromatography (absolute quantitative analysis). It was confirmed that 9.52 g (yield: 96%) of 3-[2-cyclopropyl-4-(4-fluorophenyl)-3-quinolyl]prop-2-enenitrile was produced. The organic portion was concentrated under reduced pressure, and the residue was crystallized from ethyl acetate/hexane (15/85, vol. ratio) to obtain 9.29 g (yield 88%) of 3-[2-cyclopropyl-4-(4-fluorophenyl)-3-quinolyl]prop-2-enenitrile as a yellow crystalline product (purity: 94%, measured by high performance liquid chromatography).

The obtained 3-[2-cyclopropyl-4-(4-fluorophenyl)-3-quinolyl]prop-2-enenitrile had almost the same characteristics as those described in Example 1.

EXAMPLE 6

Preparation of 3-[2-Cyclopropyl-4-(4-fluorophenyl)-3-quinolyl]prop-2-enenitrile

In a 50 mL-volume glass flask equipped with a stirrer and a thermometer were placed under argon atmosphere 1.75 g (6.01 mmol) of 2-cyclopropyl-4-(4-fluorophenyl)-quinoline-3-carbaldehyde, 2.5 mL (47.5 mmol) of acetonitrile, 13.5 mL of methylal (dielectric constant at 20° C.: 2.7), and 0.56 g (10.3 mmol) of sodium methoxide. The content was reacted at 41° C. for 9 hours. The resulting mixture was chilled in an ice bath. To the chilled mixture were slowly added under stirring 30 mL of toluene and 7.0 mL (7.00 mmol) of hydrochloric acid (1 mol/L), successively. The separated organic portion was taken out. After washing with two portions of saturated aqueous sodium chloride solution (10 mL), the organic portion was dried over anhydrous magnesium sulfate. The organic portion was then filtered and analyzed by high performance liquid chromatography (absolute quantitative analysis). It was confirmed that 1.79 g (yield: 96%) of 3-[2-cyclopropyl-4-(4-fluorophenyl)-3-quinolyl]prop-2-enenitrile was produced.

EXAMPLE 7

Preparation of 3-[2-Cyclopropyl-4-(4-fluorophenyl)-3-quinolyl]prop-2-enenitrile

In a flask similar to that of Example 6 were placed under argon atmosphere 1.74 g (5.98 mmol) of 2-cyclopropyl-4-(4-fluorophenyl)quinoline-3-carbaldehyde, 0.80 mL (15.2 mmol) of acetonitrile, 8.0 mL of tetrahydrofuran (dielectric constant at 25° C.: 7.58), and 0.41 g (7.55 mmol) of sodium methoxide. The content was reacted at 52° C. for 4.5 hours. The resulting mixture was chilled in an ice bath. To the chilled mixture were slowly added under stirring 30 mL of toluene and 7.0 mL (7.00 mmol) of hydrochloric acid (1 mol/L), successively. The separated organic portion was taken out. After washing with two portions of saturated aqueous sodium chloride solution (10 mL), the organic portion was dried over anhydrous magnesium sulfate. The organic portion was then filtered and analyzed by high performance liquid chromatography (absolute quantitative analysis). It was confirmed that 1.64 g (yield: 88%) of 3-[2-cyclopropyl-4-(4-fluoro-phenyl)-3-quinolyl]prop-2-enenitrile was produced.

INDUSTRIAL APPLICABILITY

According to the preparation method of the invention, the known 3-[2-cyclopropyl-4-(4-fluorophenyl)-3-quinolyl]prop-2-enenitrile is produced from a known quinolinecarbaldehyde derivative in a simple procedure. The quinolylacrylonitrile derivative can be effectively utilized to the known quinolylpropenal derivative.

What is claimed is:

1. A process for preparing 3-(2-cyclopropyl-4-(4-fluorophenyl)-3-quinolyl) prop-2-enenitrile which comprises the steps of:

reacting 2-cyclopropyl-4-(4-fluorophenyl)quinoline-3-carbaldehyde with acetonitrile in the presence of a base to produce a mixture of 3-(2-cyclopropyl-4-(4-fluorophenyl)-3-quinolyl) prop-2-enenitrile and 3-[2-cyclopropyl-4-(4-fluorophenyl)quinolin-3-yl]-3-hydroxy-propionitrile; and dehydrating the mixture in the presence of a dehydrating agent.

2. The process of claim 1, wherein the base is employed in an amount of 0.9 to 3.0 moles per one mole of the carbaldehyde.

3. The process of claim 1, wherein the base is a metal hydride, a metal amide, a metal alkoxide, an alkyl lithium, or a metal hydroxide.

4. The process of claim 1, wherein the base is sodium hydride, potassium hydride, calcium hydride, or sodium methoxide.

5. The process of claim 1, wherein the acetonitrile is employed in an amount of 0.9 to 100 moles per one mole of the carbaldehyde.

6. The process of claim 1, wherein the dehydrating agent is an inorganic acid, an organic acid, an organic acid ester, an amide, an organic acid anhydride, an acid chloride, a tertiary amine, or a silane compound.

7. The process of claim 1, wherein the dehydrating agent is a formic acid ester.

8. 3-[2-Cyclopropyl-4-(4-fluorophenyl)quinolin-3-yl]-3-hydroxypropionitrile.

9. A process for preparing 3-(2-cyclopropyl-4-(4-fluorophenyl)-3-quinolyl) prop-2-enenitrile which comprises the steps of:
   reacting 2-cyclopropyl-4-(4-fluorophenyl)quinoline-3-carbaldehyde with acetonitrile in the presence of a base; and
   dehydrating the resulting product in the presence of a dehydrating agent.

10. The process of claim 9, wherein the base is employed in an amount of 0.9 to 3.0 moles per one mole of the carbaldehyde.

11. The process of claim 9, wherein the base is a metal hydride, a metal amide, a metal alkoxide, an alkyl lithium, or a metal hydroxide.

12. The process of claim 9, wherein the base is sodium hydride, potassium hydride, calcium hydride, or sodium methoxide.

13. The process of claim 9, wherein the acetonitrile is employed in an amount of 0.9 to 100 moles per one mole of the carbaldehyde.

14. The process of claim 9, wherein the dehydrating agent is an inorganic acid, an organic acid, an organic acid ester, an amide, an organic acid anhydride, an acid chloride, a tertiary amine, or a silane compound.

15. The process of claim 9, wherein the dehydrating agent is a formic acid ester.

16. A method for preparing 3-(2-cyclopropyl-4-(4-fluorophenyl)-3-quinolyl) prop-2-enenitrile which comprises reacting 2-cyclopropyl-4-(4-fluorophenyl)quinoline-3-carbaldehyde with acetonitrile in an organic solvent in the presence of a base.

17. The method of claim 16, wherein the organic solvent has a dielectric constant of 10 or less in the temperature range of 20 to 25° C.

18. The method of claim 17, wherein the organic solvent having a dielectric constant of 10 or less in the temperature range of 20 to 25° C. is an aromatic solvent or ether solvent.

19. The method of claim 16, wherein the base is an alkoxide of an alkali metal or an alkaline earth metal.

20. The method of claim 16, wherein the reaction is performed in the temperature range of 40 to 120° C.

* * * * *